US012672914B2

(12) United States Patent
Mirkov et al.

(10) Patent No.: US 12,672,914 B2
(45) Date of Patent: Jul. 7, 2026

(54) DEVICE FOR REAL-TIME NON-CONTACT SKIN TEMPERATURE MEASUREMENT

(71) Applicant: CYNOSURE, LLC, Westford, MA (US)

(72) Inventors: Mirko Georgiev Mirkov, Chelmsford, MA (US); James Boll, Montclair, NJ (US)

(73) Assignee: CYNOSURE, LLC, Westford, MA (US)

( * ) Notice: Subject to any disclaimer, the term of this patent is extended or adjusted under 35 U.S.C. 154(b) by 199 days.

(21) Appl. No.: 18/288,138

(22) PCT Filed: Apr. 27, 2022

(86) PCT No.: PCT/US2022/026460
§ 371 (c)(1),
(2) Date: Oct. 24, 2023

(87) PCT Pub. No.: WO2022/232220
PCT Pub. Date: Nov. 3, 2022

(65) Prior Publication Data
US 2024/0197397 A1     Jun. 20, 2024

Related U.S. Application Data

(60) Provisional application No. 63/280,733, filed on Nov. 18, 2021, provisional application No. 63/180,454, filed on Apr. 27, 2021.

(51) Int. Cl.
*A61B 18/20*     (2006.01)
*A61B 18/00*     (2006.01)
(52) U.S. Cl.
CPC .. *A61B 18/203* (2013.01); *A61B 2018/00458* (2013.01); *A61B 2018/00476* (2013.01);
(Continued)

(58) Field of Classification Search
CPC ........ A61B 18/203; A61B 2018/00458; A61B 2018/00476; A61B 2018/00714;
(Continued)

(56) References Cited

U.S. PATENT DOCUMENTS 3,335,716 A     8/1967   Alt et al.
6,511,475 B1 *  1/2003   Altshuler ............. A61B 18/203
                                                      606/2
(Continued)

FOREIGN PATENT DOCUMENTS

CN     109 405 996 A     3/2019
JP     2001 004460 A     1/2001

OTHER PUBLICATIONS

PCT International Search Report and PCT Written Opinion for PCT International Application No. PCT/US2022/026460; date of mailing Aug. 25, 2022; (9 pages).
(Continued)

*Primary Examiner* — Ahmed M Farah
(74) *Attorney, Agent, or Firm* — K&L GATES LLP

(57)     ABSTRACT

In part, the disclosure relates to an electromagnetic radiation (EMR) delivery system for non-invasive surface tissue temperature monitoring. The system includes a first source of EMR having a first wavelength range; a second source of EMR having a second wavelength range; and a tissue contacting material comprising a set of wavelength range specific EMR responsive dopants. In various embodiments, the tissue contacting material is positioned on a surface of a target region of tissue, wherein the tissue contacting material receives EMR from the first source, wherein the tissue contacting material receives EMR from the second source. The first and second sources may be arranged in different orientations or along a common axis or orientation.

14 Claims, 5 Drawing Sheets

(52) U.S. Cl.
CPC ............... *A61B 2018/00714* (2013.01); *A61B 2018/00791* (2013.01); *A61B 2018/00898* (2013.01); *A61B 2018/2065* (2013.01)

(58) Field of Classification Search
CPC ........... A61B 2018/00791; A61B 2018/00898; A61B 2018/2065
USPC .............................................................. 606/9
See application file for complete search history.

(56) References Cited

U.S. PATENT DOCUMENTS

| | | | | |
|---|---|---|---|---|
| 8,105,322 | B2 * | 1/2012 | Ely | A61B 18/203 606/9 |
| 8,346,347 | B2 * | 1/2013 | Altshuler | A61B 5/6843 600/476 |
| 11,684,799 | B2 * | 6/2023 | Hunziker | G16H 20/40 607/89 |
| 2002/0045922 | A1 | 4/2002 | Nield et al. | |
| 2007/0060819 | A1 * | 3/2007 | Altshuler | A61B 5/444 600/475 |
| 2009/0069741 | A1 * | 3/2009 | Altshuler | A61N 1/327 606/33 |
| 2009/0234338 | A1 * | 9/2009 | Roth | A61B 18/203 606/9 |
| 2009/0234342 | A1 * | 9/2009 | Ely | A61B 18/203 606/9 |
| 2009/0234343 | A1 * | 9/2009 | Behrakis | A61B 18/203 606/9 |
| 2012/0283575 | A1 * | 11/2012 | Rao | A61B 5/015 600/476 |
| 2013/0079661 | A1 | 3/2013 | Tolosa et al. | |
| 2013/0096546 | A1 * | 4/2013 | Mirkov | A61B 18/22 606/9 |
| 2013/0278226 | A1 | 10/2013 | Cong et al. | |
| 2016/0287225 | A1 | 10/2016 | Sharonov | |
| 2019/0216335 | A1 | 7/2019 | Stepien | |
| 2019/0388151 | A1 * | 12/2019 | Bhawalkar | A61B 5/4836 |
| 2022/0211436 | A1 * | 7/2022 | Milner | A61B 18/203 |
| 2022/0401750 | A1 * | 12/2022 | Daly | A61N 5/0616 |

OTHER PUBLICATIONS

Extended European Search Report for European Patent Application No. 25163968.8 mailed from the European Patent Office on May 23, 2025 (8 pages).

* cited by examiner

Control system

Fluorescent excitation source

Treatment beam source

Fluorescent signal detection system

FnPG

Epidermis

Dermis

DEVICE FOR REAL-TIME NON-CONTACT SKIN TEMPERATURE MEASUREMENT

CROSS REFERENCE TO RELATED APPLICATIONS

This is the national phase under 35 U.S.C. § 371 of International Application No. PCT/US2022/026460 filed on Apr. 27, 2022, which claims priority to and the benefit of U.S. Provisional Application Nos. 63/180,454 filed on Apr. 27 2021 and 63/280,733 filed on Nov. 18, 2021, the entire disclosures of each of which are incorporated by reference herein.

BACKGROUND

The treatment of several dermatological indications uses energy delivery at various depths in the dermis using various types of devices and systems. For example, such dermatological indications include the removal of unwanted hair, unwanted vascular lesions, or dermal pigmented lesions. In most cases it is desirable to preserve the epidermis during these dermatological treatments. The epidermis contains chromophores such as melanin and water that can impede the delivery of light to deeper targets while generating undesired heat leading to an undesirable epidermal temperature rise. Existing approaches to avoid epidermal temperature rise during such dermatological energy-based treatments is based on epidermal cooling that has taken various forms—blowing cold air on the epidermis, exposing the epidermis to cryogen or contact cooling the epidermis. Cold air cooling may be used after application of an optically transparent gel on the skin of the surface to serve as a cold heat sink during energy based (e.g., light based or laser) treatments.

SUMMARY

In part, the disclosure relates to an electromagnetic radiation (EMR) delivery and monitoring system for non-invasive surface tissue temperature monitoring. The system may include a first source of EMR having a first wavelength range; a second source of EMR having a second wavelength range; and a tissue contacting material comprising a set of wavelength range specific EMR responsive dopants, wherein the tissue contacting material is positioned on a surface of a target region of tissue, wherein the tissue contacting material receives EMR from the first source at a first orientation, wherein the tissue contacting material receives EMR from the second source at a second orientation.

In one embodiment, the first orientation and the second orientation are the same. In one embodiment, the second orientation is at an angle relative to the first orientation. In one embodiment, the angle ranges from about 5 degrees to about 85 degrees. In one embodiment, the angle is about 45 degrees. In one embodiment, the first source of EMR generates a treatment beam.

In one embodiment, the first wavelength range of treatment beam is from about 500 nm to about 5000 nm or falls without this range. In one embodiment, the second source of EMR generates an excitation beam. In one embodiment, the second wavelength range of the excitation beam is from about 400 nm to about 2500 nm or falls within this range. In one embodiment, the second source of EMR is operable to transmit a second wavelength and one or more additional wavelength bands.

In one embodiment, the EMR responsive dopants are selected from the group consisting of a particle, a bead, a layer, a thin film, a fluorescent material, a fluorescent nanoparticle, an upconversion fluorescent nanoparticle, an upconversion material, a nanoparticle, a chromophore, a scattering element, a refracting element, a wavelength shifting material or device, interference generator, absorber and combinations thereof.

In one embodiment, the EMR responsive dopants comprise two or more fluorescent materials. In one embodiment, the tissue contacting material is a heatsink, a gel, a solution, or material operable to transmit EMR within the first wavelength range. In one embodiment, the EMR responsive dopant emits or transmits EMR having a temperature dependent wavelength that ranges from about 400 nm to about 5000 nm or falls within that range. In one embodiment, the tissue contacting material is a sapphire heatsink, aqueous gel or solution and the dopant is a group of fluorescent particles.

In one embodiment, the concentration of dopant per unit volume is selected to provide sufficient signal to enable detection and to avoid self-extinguishing. In one embodiment, the system further includes a signal detector, wherein the signal detector is positioned to receive temperature dependent EMR generated from one or more of the dopants. In one embodiment, the system further includes a signal processor, wherein the signal processor is operable to measure temperature changes using received temperature dependent EMR from one or more dopants and one or more parameters of the EMR generated from the second EMR source.

In one embodiment, the EMR responsive dopants are temperature sensitive such that tissue temperature changes cause changes in EMR emitted or transmitted from the dopants. In one embodiment, the system further includes a control system operable to stop treatment or generate an alarm when a tissue temperature exceeding a threshold or predetermined value has been detected using EMR from the dopants. In one embodiment, the tissue contacting material is a tissue contacting gel or tissue contacting solution.

In part, the disclosure relates to methods, systems and devices configured to compensate for the contribution of room lights or treatment lights when using temperature dependent EMR. In one embodiment, the system further includes a wavelength selective filter disposed in front of the detector and configured to filter one or more wavelength bands of room or treatment radiation while transmitting the temperature dependent EMR generated from one or more of the dopants. In one embodiment, the second source of EMR generates an excitation beam, wherein the excitation beam has a modulation frequency $f_m$. In one embodiment, the system further includes a lock-in amplifier having a reference frequency, wherein the reference frequency is the modulation frequency $f_m$. In one embodiment, the lock-in amplifier is configured to increase signal to noise ratio of the temperature dependent EMR generated from one or more of the dopants. In one embodiment, $f_m$ ranges from about 100 Hz to about 100 kHz. In one embodiment, the power of excitation beam ranges from about 5 W/cm$^2$ to about 30 W/cm$^2$. In one embodiment, the second source of EMR generates a pulsed excitation beam and the first source of EMR generates a treatment beam. In one embodiment, the first wavelength range of treatment beam is from about 500 nm to about 5000 nm.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various apparatus, optical elements, dopants, optical paths, waveguides, optically reactive chemical agents or particles, EMR responsive dopants, electro-optical devices, inputs, outputs, ports, channels, components and parts of the foregoing disclosed herein can be used with any laser, laser-based treatment system, EMR source, cooling system, waveguide, control system, monitoring system, fiber, transmitter, transceiver, receiver, and other devices and systems without limitation.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

The structure and function of the disclosure can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

Figure 1:
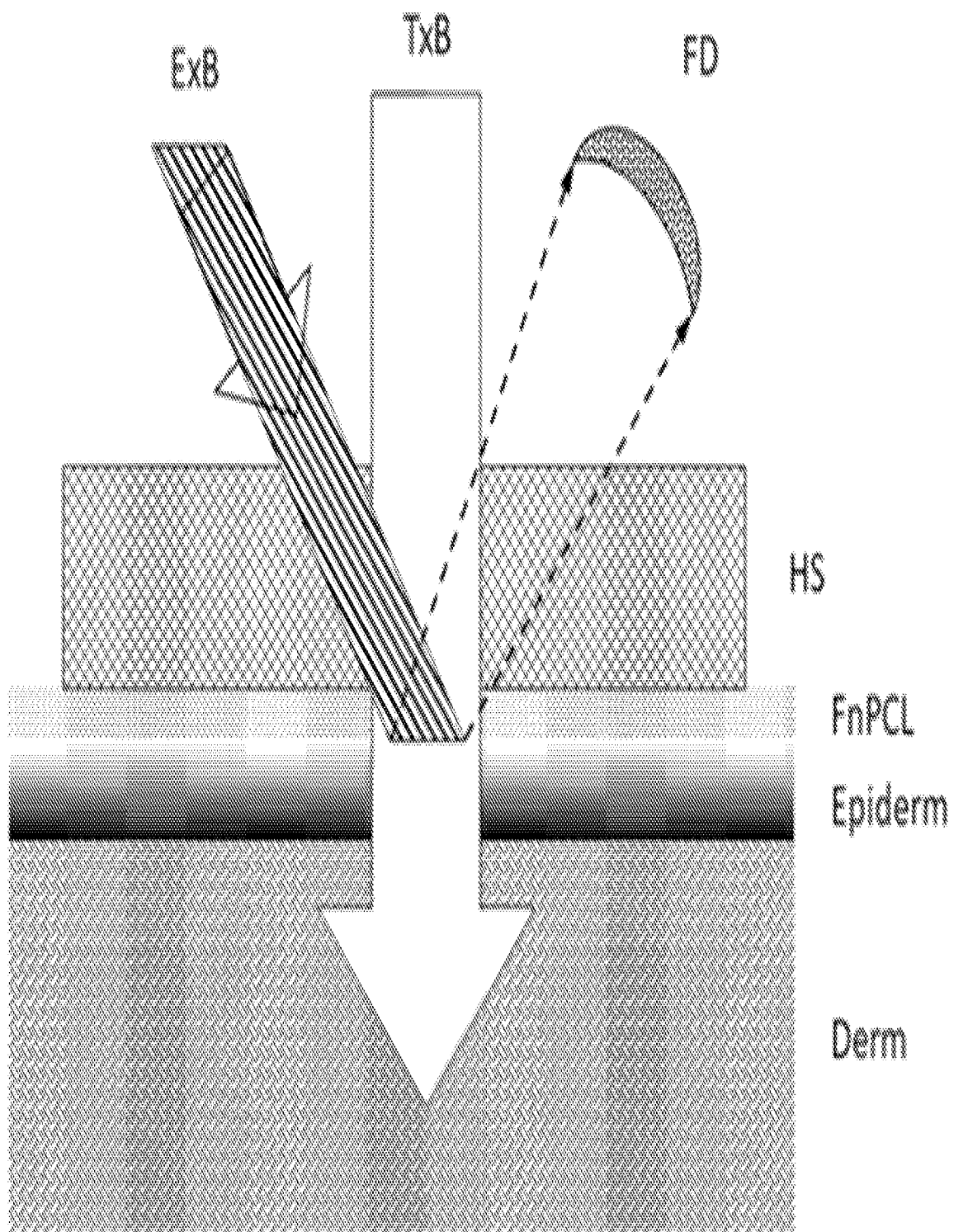
FIG. 1 is a schematic diagram of an exemplary EMR delivery system suitable for performing real time temperature monitoring of a tissue region according to an illustrative embodiment of the disclosure.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

Applicants submit that real time temperature monitoring of the skin before, during and after every energy-based treatment (e.g., light based or laser) exposure would be the ultimate safety feature for an energy-based skin treatment. The main goal of epidermal cooling during energy-based treatment is protection of the epidermis with a minimal, or insignificant, impediment to the energy delivery to biological targets in the dermis or other tissue. Epidermal injury may be correlated with the temperature rise in the epidermis and the time period that the epidermal tissue has been maintained at that increased or raised temperature. The relationship between tissue injury, temperature rise and duration of sustained raised temperature period is highly non-linear. The non-linear dependence necessitates that the temperature changes in the epidermis are followed in real time to pause, lessen, or terminate energy delivery when the tissue temperature exceeds a safety threshold.

For example, a laser hair removal pulse may have a pulse duration between about 5 ms and about 300 ms. The practitioner may choose the pulse duration based on the patient skin type, hair follicle diameters and observed skin response. A temperature monitoring system would need to have sufficiently fast response for any choice of a pulse duration in the range from about 5 ms to about 300 ms. For such pulses, epidermal temperature should be monitored on a time scale that is comparable and/or shorter than the laser pulse duration, for example measurement occurs on a time scale of 1 ms or less for a treatment having about 5 ms laser pulse duration, or from 0.1 ms to 1 ms for the 5 ms pulse duration. In another example, pulse durations can range from about 5 ms to about 300 ms monitoring the skin temperature on a time scale of about 0.1 to about 2 ms would be sufficient. Such speed is possible with high-end IR temperature sensors and cameras; however, it comes with a high cost and complexity. IR does raise various challenges that are circumvented with various embodiments of the disclosure by avoiding undesirable IR wavelength ranges for temperature dependent EMR signal detection.

A transparent contact cooling device placed in contact with a target region of the tissue such as one or more skin layers during the energy delivery generally precludes using commercially available IR temperature sensors and cameras. Typically, IR temperature sensors operate at wavelengths between about 8 μm and about 14 μm for sensing tissue temperatures between about 0° C. and about 100° C. Commonly used transparent heat sink materials like sapphire and water-based gels have low transmission in the wavelength range between about 8 and about 14 μm. That makes most transparent heat sink materials incompatible with most commercially available IR temperature sensors and cameras. The concept summarized in the present application describes a real-time skin temperature monitoring system that works through transparent tissue contacting heat sinks (or cooling devices) like sapphire and water-based gels and avoids the use of IR temperature sensors operating in the wavelength range between about 8 and about 14 μm where the contact heat sinks have low transmission. In various embodiments, the systems and methods use EMR responsive dopants or materials that emit or generate EMR correlated with tissue temperature changes outside the IR wavelength range. Other EMR parameters and phenomena may be used to measure temperature based on the use of EMR responsive dopants.

Before the delivery of each treatment pulse, or pulse sequence, the proposed real time temperature monitoring system can evaluate if the pretreatment cooling has brought the epidermal temperature to a safe range. If the pretreatment epidermis temperature is out of the safe range, the system can alert the operator and identify possible cooling malfunction or improper operator technique, like for example insufficient pre-cooling contact time. During the delivery of a relatively long treatment pulse, or a multi pulse sequence, the real time temperature monitoring system can evaluate if the gradually rising epidermal temperature is staying within a safe range or is driving toward the unsafe or damage range. The real time temperature monitoring system can evaluate if the epidermal temperature is rising such that it exceeds set trigger points identifying a safe range. Further, once the set trigger point for a safe temperature range is exceeded, the system can be enabled to alert the operator and/or pause, change, or terminate the pulse sequence.

In an exemplary system, after the delivery of each pulse, or pulse sequence, the real time temperature monitoring system evaluates if the skin temperature rise is within the expected safe range. The temperature monitoring system will alert the operator if the temperature is approaching the upper boundary of the safety range. In some embodiments, the temperature monitoring system will communicate in real-time with the treatment system so the treatment system (or monitoring system or a control system) will stop (or pause) further pulse delivery if the temperature exceeds the upper boundary of the safety range and the operator will be alerted. In other embodiments, the temperature monitoring systems of the treatment system may be operable to generate alerts or to stop operation of the treatment system in response to one or more temperature values, thresholds or ranges.

Some laser-based devices may use contact cooling via sapphire or contact cooling via a cold gel or solution applied to the skin surface combined with cold air cooling. In both cases the upper surface of the epidermis is in contact with an optically transparent heat sink. This heat sink may include one or more of cold sapphire and/or cold topical (e.g., cold gel) or other optically transparent materials with heat absorbing or heat conducting properties. Contact cooling via sapphire employs a water-based contact liquid deposited on the skin to improve the thermal contact of the skin surface with the cold sapphire. Contact cooling via cold gel employs a cold gel spread over a region of the skin before treatment. The cold gel may be water-based in various embodiments. The gel may be pre-cooled to below normal skin temperature by keeping it at room temperature or keeping it in a refrigerator or freezer before the spreading on the skin. The gel may be pre-cooled during the energy-based treatment by directing some of a cold air flow to areas of the skin intended to be treated next. The gel may be parallel- and/or post-cooled during the energy-based treatment by directing some portion of the cold air flow to areas of the skin exposed to electromagnetic radiation (EMR) and/or directing some portion of the cold air flow to areas of the skin after they were treated. As an example, the temperature of the cold air flow can be in the range between about −40° C. and about 10° C., more preferably between about −20° C. and about −10° ° C. In both cases the treatment beam is delivered through the optically transparent heat sink. Both optically transparent heat sinks have low transmission in the wavelength range for IR temperature measurements and prevent the direct non-contact measurement of the epidermis temperature for example with an IR temperature sensor or IR camera.

In various embodiments, EMR responsive materials such as fluorescent material(s) or other materials are added to, disposed on or used with a contact medium, material, EMR transmissive wave guide, thin film or layer, or other devices, gels, creams, topicals, medicaments, or tissue cooling apparatus or structures. The EMR responsive materials provide a mechanism for temperature monitoring using EMR that is not dependent on IR-based detectors. For example, in one embodiment fluorescent material(s) is used with an optically transparent heat sink applied to the skin surface. The various EMR responsive materials disclosed herein may be mixed with, disposed on in, dispersed in or on, or otherwise combined or integrated with various aqueous or other gels/substrates, heatsinks and various apparatus, lenses, structures and devices. In one embodiment, fluorescent based material(s) is incorporated into a water-based contact liquid or into a cold gel in contact with the skin surface, which will allow for non-contact temperature measurement of the skin surface without an IR temperature sensor.

In various embodiments, emission of light from a substance that does not arise from heating and occurs following the absorption of light is the basis for the EMR dopants generating temperature dependent EMR. Various materials disclosed herein that exhibit luminescence, or photoluminescence may be used. Fluorescence is a photoluminescence process that occurs fast after the absorption of light through a singlet state transition. The fluorescent material is incorporated into the contact medium or heatsink, for example, the fluorescent material may be encapsulated within nanoparticles or other convenient carrier that makes it safe for topical application on human skin. In addition, to avoid unwanted heating, the fluorescent material in the contact medium must have low absorption at the wavelength of the treatment laser. In some embodiments, EMR transparent or substantially transparent or wavelength selective materials such as thermally absorbing or insulating or conducting materials may also be used in conjunction with the EMR responsive dopants disclosed herein.

Real time temperature monitoring through an optically transparent heat sink based on temperature dependent fluorescence FIG. 1 is a schematic diagram of an exemplary EMR delivery system suitable for performing real time temperature monitoring using a heatsink and one or more EMR responsive materials. In various embodiments, the EMR delivery system may use a heatsink material or device such as for example, a sapphire heatsink that includes or works in conjunction with an EMR responsive material such as material that exhibits temperature dependent fluorescence or other detectable EMR changes, such as interference, wavelength shifting, phase changes and others. In FIG. 1, various exemplary tissues including the dermis (Derm) and epidermis (Epiderm) are shown. These and other tissues may be treated or otherwise energized or modified using EMR. Various tissues may be monitored for temperature changes using a signal generated in response to a change in one or more properties of an EMR responsive dopant or other material positioned relative to a target tissue region of interest. In part, the disclosure relates to systems and methods of real time temperature monitoring through a heatsink with epidermis contact liquid/contact material that includes EMR responsive materials such as fluorescent nanoparticles or other materials or combinations as disclosed herein.

In some embodiments, a contact liquid, gel or other material that includes an EMR responsive material such as fluorescent nanoparticles is shown. This EMR responsive material or dopant for use with another material or as a layer is identified as FnPCL in FIG. 1. A transparent heatsink HS is also shown. The heatsink HS may include sapphire or other EMR transmitting material. In some embodiments, a region or layer of the HS may include EMR responsive material in lieu of the FnPCL or in addition to it.

In addition, a first EMR source and a second EMR source are used to generate a first beam and a second beam. In some embodiments, one EMR source is used in conjunction with a beam splitter and other optical elements to change an initial beam into a first beam and a second beam having different wavelengths.

In one embodiment, one of the EMR beams is a treatment beam TxB and the other beam is an excitation beam ExB. In some embodiments, the excitation beam ExB is a fluorescent excitation beam. In various embodiments, the EMR delivery system also includes a signal detector FD. The signal detector FD may be operable to detect fluorescent signals such as those from the FnPCL. The signal detector may be operable to detect other signals from EMR responsive dopants and materials. A signal conditioning optical system may be used as a separate system or may be combined or in optical or electrically communication with the signal detector FD. The signal detector and a signal processor may be combined as part of a control system to generate alerts or terminate treatment beam generation in various embodiments.

Figure 2:
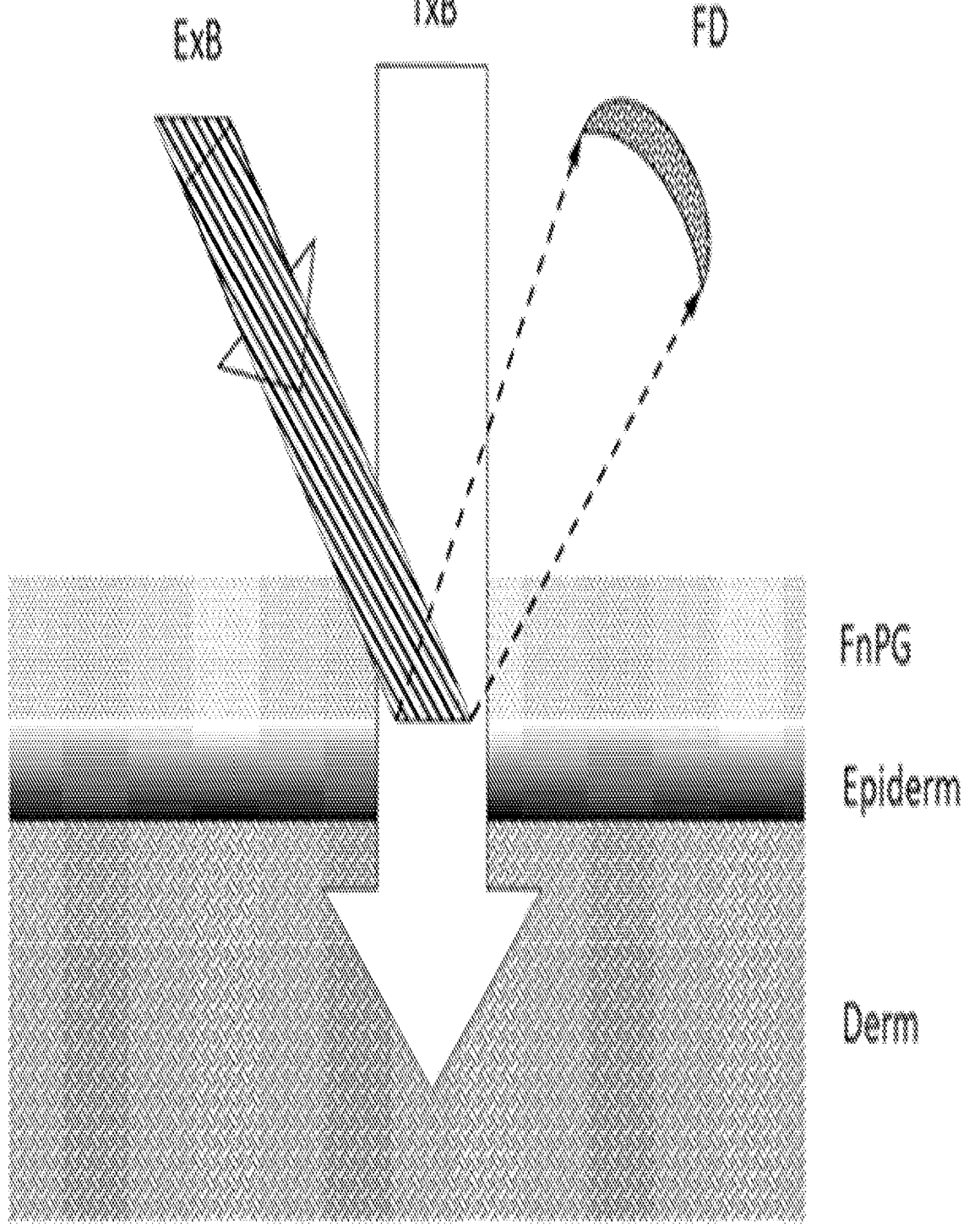
FIG. 2 is a schematic diagram of an exemplary EMR delivery system suitable for performing real time temperature monitoring of a tissue region according to an illustrative embodiment of the disclosure.

FIG. 2 is a schematic diagram of a system for directing EMR to tissue while simultaneously performing a real time temperature monitoring using a first EMR source and a second EMR source. In FIG. 2, various exemplary tissues including the dermis (Derm) and epidermis (Epiderm) are shown. These and other tissues may be treated or otherwise energized or modified using EMR. Various tissues may be monitored for temperature changes using a signal generated in response to a change in one or more properties of an EMR responsive dopant or other material positioned relative to a target tissue region of interest. In various embodiments, real time temperature monitoring through a cold gel, topical, or other material that includes fluorescent EMR dopants such as nanoparticles may be used.

As shown in FIG. 2, the real time temperature monitoring is performed through a cold gel using temperature dependent fluorescence. A solution or gel containing fluorescent nanoparticles is shown as FnPG. In one embodiment, one of the EMR beams is a treatment beam TxB and the other beam is an excitation beam ExB. In some embodiments, the excitation beam ExB is a fluorescent excitation beam. In various embodiments, the EMR delivery system also includes a signal detector FD. The signal detector FD may be operable to detect fluorescent signals such as those from the FnPG. The signal detector may be operable to detect other signals from EMR responsive dopants and materials. A signal conditioning optical system may be used as a separate system or may be combined or in optical or electrically communication with the signal detector FD. In some embodiments, a filter such as a wavelength selective filter may be positioned in front of the detector FD (not shown). The wavelength selective filter may be configured to filter out light of one or more wavelengths that would otherwise decrease the accuracy of the fluorescent signal impinging on the detector FD. The signal detector and a signal processor may be combined as part of a control system to generate alerts or terminate treatment beam generation in various embodiments. Although a device or assembly for delivering cold air flow to the cold gel is not shown on FIG. 2, various fans, blowers, and other coolers can be used in various embodiments as a pre, during, and post treatment.

In both cases, cold sapphire or cold gel contact cooling, it is preferable for the fluorescence excitation beam to irradiate the epidermal region, in thermal contact with the carrier containing the fluorescent nanoparticles, where the treatment beam enters the epidermis, as shown in the exemplary systems and methods depicted in FIGS. 1 and 2. That region will reach the highest epidermal temperature rise when compared to the surrounding epidermis not irradiated by the treatment beam. The measured highest temperature rise or other measurements or values obtained or derived from an EMR signal may be used to evaluate epidermal safety such as by performing real time tissue temperature monitoring. In various embodiments, the EMR signal generated in response to incident EMR to one or more optically responsive elements is processed to obtain temperature information relative to tissue in thermal communication with the optically responsive element. The optically responsive element may include one or more fluorescent beads or particles such as nanoparticles, fluorophores, chromophores, or other dopants disposed on or in the cold gel or other optical transparent structure or cooling material or apparatus disclosed herein. In some embodiments, rare-earth doped upconversion nanoparticles (UCNPs) may be used in various embodiments. The fluorescent nanoparticles irradiated by the excitation beam will emit one or more temperature dependent optical signals in all directions. A fraction of that optical signal will be captured by the fluorescent signal detector with its signal conditioning optical system, FD. The fluorescent signal can be monitored continuously, digitized as needed, and used to control the treatment beam delivery in real time to maintain epidermal safety.

The fluorescence excitation beam and treatment beam geometry outlined in exemplary embodiments depicted in FIG. 1 and FIG. 2 are only representative examples and do not exclude other embodiments. In various embodiments, the excitation beam and treatment beam may be arranged coaxially or substantially coaxially. For example, in some embodiments a wavelength or polarization based beam combiner may be used to deliver an excitation beam coaxially or substantially coaxially with the treatment beam such that tissue treatment and excitation or stimulation of EMR responsive dopants in optical path of such beams may be caused to fluoresce or undergo another optical or EMR transition such as an upconversion. In various embodiments, methods of treating tissue and monitoring temperature may be performed simultaneously or substantially simultaneously.

The fluorescent nanoparticles irradiated by the excitation beam, coaxial with the treatment beam, will emit one or more temperature dependent optical signals in all directions and a fraction of that optical signal will be captured by the fluorescent signal detector. A further example may be envisioned where a fluorescent material is selected so that the wavelength of the treatment beam makes it suitable also as a fluorescent excitation beam. Such modes of operation may be based on fluorescent emission following a single or double or multiple photon absorption or upconversion. The tissue damage in the epidermis can be correlated with an integral of the Arrhenius type process of damage accumulation as a function of the time spent at elevated temperature. Alternatively, the tissue damage in the epidermis can be evaluated in a clinical study with escalating fluence delivery and measurement of the peak epidermal temperature at the end of the pulse, or pulse sequence. Then the clinical evaluation of epidermis tissue damage at about 10 min, about 1 hour and about 24 hours post treatment can be correlated with the measured peak epidermal temperature and identify ranges of peak temperature rises that are safe and leave the epidermis with minimal or no tissue damage.

The exemplary EMR delivery and temperature monitoring systems depicted in FIGS. 1 and 2 may use a single fluorescent detector to capture representative peak temperature in the epidermal region irradiated by the treatment beam and the excitation beam. Alternatively, a multichannel fluorescent detector, like a CCD camera, can capture a 2D thermal map of the epidermal temperature in the treatment beam region and the surrounding area.

Fluorescent Thermometers

Non-contact thermometers based on fluorescence or luminescence have been an ongoing area of development. The fluorescence light emission is affected by changes in the temperature in the surrounding medium. Changes in the fluorescence light emission are correlated with temperature changes in the tissue region being monitored. In various embodiments, the tissue being treated heats up which heats the carrier materials (gel, solution, heatsink, other materials) that the EMR responsive dopants are in thermal communication with and thus operable to emit light correlated with tissue temperature changes. For example, temperature changes may be measured using changes in one or more of the following parameters:

i. The changes in intensity of a single transition or a pair of transitions ii. The spectral shift or bandwidth change of a single transition iii. The intensity decay versus time profile of a single or multiple transitions Single transition intensity is rarely used for temperature monitoring due to intensity variations introduced in transmission through multiple optical interfaces. A pair of selected transition intensities allows one to use the ratio of the two intensities for temperature monitoring. Taking the ratio of the two intensities approximately cancels out the transmission variations.

The thin layer of water-based contact liquid between the skin and the cold sapphire will have an approximately uniform spatial temperature profile across its thickness. Its temperature will vary during the laser pulse delivery due to heat generation in the melanin layer in the epidermis and heat diffusion into the cold sapphire heat sink. During the laser pulse delivery, a fluorescent material in the contact liquid can be illuminated by an excitation source such as an LED or continuous wave source with a preferred wavelength. Taking the ratio of two fluorescent line intensities may be used to perform the monitoring of the temperature of the contact liquid in real time. The temperature of epidermal melanin can be calculated based on the known thermal diffusivity of the contact liquid and the epidermis.

Temperature Responsive Material Selection and Related Properties

In various embodiments, the fluorescent material selected for the contact liquid or gel includes or substantially complies with one or more of the following properties or criteria for selection for temperature monitoring and other features and embodiments disclosed herein.

1. Material with temperature dependent fluorescent intensity at two transitions with ratio that can be related to absolute temperature or relative temperature rise from initial base level.

a. Such materials exist, for example, Nd:YVO4 and Nd:YALO3, which both have two line temperature dependent fluorescence in BW-II—between about 1000 nm and about 1350 nm. Unfortunately, both materials are used for laser crystals with large absorption at pump wavelengths between about 790 nm to about 815 nm and that makes them unsuitable for fluorescence temperature measurements during laser treatment with about 800 nm laser.

2. The temperature range of interest of the fluorescent material has a favorable signal to noise ratio at the temperature range between about −10° C. and about 90° ° C., or more preferably between about 5 and about 70° C.

3. Some exemplary fluorescent materials can include, fluorescent nanoparticles, fluorescent upconversion nanoparticles, fluorescent nano emulsions, fluorescent liposomes, fluorescent encapsulated materials, fluorescent material in powdered or granular form mixed with a carrier before application, or fluorescent materials carried within a film.

4. Suitable fluorescent materials could be organic or inorganic.

5. Optionally, the fluorescent material is encapsulated in nanoparticles or another convenient carrier that makes it biocompatible and hypoallergenic for topical application on human skin.

6. The particles of fluorescent material follow the temperature changes in the surrounding medium and emit representative fluorescence signal with a delay of less than about 10 milliseconds, or preferably less than about 1 millisecond.

7. The two fluorescent transitions are at wavelengths longer than about 690 nm. In some embodiments, these are selected to avoid fluorescence of skin tissue including melanin or other skin tissues. Where the fluorescence intensity is larger, for example, about 10× larger than the skin tissue endogenous fluorescence, and it may be acceptable to have fluorescent transitions at wavelengths shorter than about 690 nm if the temperature dependent fluorescence intensity is much larger.

8. The targeted fluorescence material excitation wavelength should be longer than about 450 nm to avoid UV skin exposure and this matches one or more candidate LED sources. More preferably the wavelength is longer than about 550 nm to avoid excitation of melanin fluorescence in the epidermis.

9. The targeted fluorescence material has negligible absorption at any targeted treatment wavelength, for example, where the treatment wavelength is between about 790 nm and about 815 nm. The optical band about 790 nm to about 815 nm overlaps with the expected wavelength range of the treatment laser. If the fluorescence material absorbs the treatment laser wavelength to the extent that self-heating would affect the temperature measurements of the skin, so this is undesirable and is to be avoided. In another example, where the treatment wavelength is between about 1040 nm and about 1080 nm, the optical band from about 1040 nm to about 1080 nm overlaps with the expected wavelength range of the treatment laser. If the fluorescence material absorbs the treatment laser wavelength, self-heating would affect the temperature measurements of the skin, so this is undesirable and is to be avoided.

Various materials maybe used that satisfy or partially satisfy the requirements in the list of desired properties. Nd:YVO$_4$ and Nd:YALO$_3$ both have two line temperature dependent fluorescence in BW-II—between about 1000 and about 1350 nm. Unfortunately, both materials are used for laser crystals with large absorption at pump wavelengths between about 790 to about 815 nm and that makes them unsuitable for fluorescence temperature measurements during laser treatment with about 800 nm laser.

Cold gel combined with cold air cooling is used commercially in the Alexandrite and Nd:YAG hair removal lasers. Fluorescent temperature sensitive material can be added to the cold gel in contact with the skin. The cold gel layer applied to the skin surface before treatment is relatively thick on the order of about 1 mm to about 5 mm. Fluorescent material in the gel close to the epidermal surface will emit light representative of the epidermal temperature. Fluorescent material in the gel close to the external surface exposed to the flow of cold air will emit light representative of the much cooler air-gel boundary. A fluorescent material that increases its emission bandwidth of a single transition or shifts its spectrum as a function of the temperature increase would be suitable to produce fluorescent measurement representative of the highest temperature in the material.

An example list of desired properties for a fluorescent material for the cold gel, heatsink, or other EMR responsive dopant includes:

1. Material with temperature dependent fluorescent spectral shift or bandwidth that can be related to absolute temperature or relative temperature rise from initial base level.
2. The temperature range of interest of the fluorescent material has a favorable signal to noise ratio at the temperature range between about −10 and about 90° ° C., or more preferably between about 5 and about 70° C.
3. Some exemplary fluorescent materials can include, fluorescent nanoparticles, fluorescent upconversion nanoparticles, fluorescent nano emulsions, fluorescent liposomes, fluorescent encapsulated materials, fluorescent material in powdered or granular form mixed with a carrier before application, or fluorescent materials carried within a film.
4. Suitable fluorescent materials could be organic or inorganic.
5. Optionally, the fluorescent material is encapsulated in nanoparticles or another convenient carrier that makes it biocompatible and hypoallergenic for topical application on human skin.
6. The particles of fluorescent material follow the temperature changes in the surrounding medium and emit representative fluorescence signal with a delay of less than about 10 milliseconds, or preferably less than about 1 millisecond.
7. The two fluorescent transitions are at wavelengths longer than about 690 nm these are selected to avoid fluorescence of skin tissue including melanin or other skin tissues. Where the fluorescence intensity is larger, for example, about 10× larger than the skin tissue endogenous fluorescence, and it may be acceptable to have fluorescent transitions at wavelengths shorter than about 690 nm if the temperature dependent fluorescence intensity is much larger.
8. The targeted fluorescence material excitation wavelength should be longer than about 450 nm to avoid UV skin exposure and this matches LED sources. More preferably the wavelength is longer than about 550 nm to avoid excitation of melanin fluorescence in the epidermis.
9. The targeted fluorescence material has negligible absorption between about 750 and about 765 nm and at about 1064 nm. The optical band about 750 to about 765 nm and about 1064 nm wavelength overlap with the expected wavelength ranges of treatments using Alexandrite and Nd:YAG lasers. If the fluorescence material absorbs the treatment laser wavelength to the extent that self-heating would affect the temperature measurements of the skin, so this is undesirable and is to be avoided.

One or more of the foregoing properties may be used to select various classes of EMR responsive dopants. Nd:YALO$_3$ has temperature dependent fluorescence bandwidth in BW-I—between about 700 and about 950 nm. Unfortunately, the material has large absorption between about 750 and about 760 nm and that makes it unsuitable for fluorescence temperature measurements during laser treatment with the Alexandrite laser.

In various embodiments, a material that exhibits upconversion in response to EMR may be selected as an EMR responsive dopant alone or in combination with other EMR responsive dopants, carriers, and other materials. For example, an upconversion based temperature dependent fluorescent material with negligible absorption in the treatment laser bands about 750 nm to about 765 nm, about 790 nm to about 815 nm and about 1040 nm to about 1080 nm may be selected as an EMR responsive dopant in some embodiments. In some embodiments, an exemplary EMR responsive dopant may include combinations of one or more of Ytterbium, Erbium, Sodium, and Yttrium, Fluoride, and Fluorine.

Figure 3:
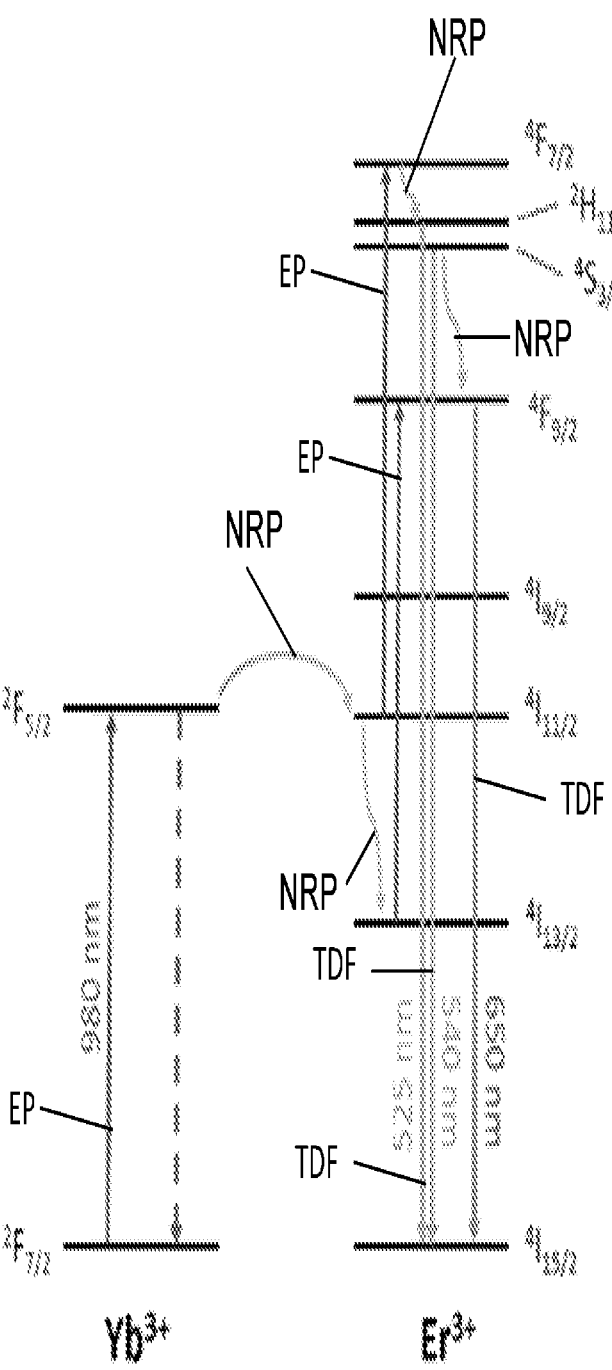
FIG. 3 is a schematic diagram of an exemplary upconversion mechanism for an EMR dopant suitable for supporting real time temperature monitoring according to an illustrative embodiment of the disclosure.

The temperature dependent fluorescent material Ytterbium and Erbium doped Sodium yttrium fluoride, $NaY_{0.77}Yb_{0.20}Er_{0.03}F_4$, has absorption and emission energy level diagram that is shown in FIG. 3. This material and variants thereof may be used as an EMR responsive dopant in various embodiments. In FIG. 3, an exemplary upconversion mechanism is shown for an EMR responsive dopant. The upconversion mechanism is shown for $NaY_{0.77}Yb_{0.20}Er_{0.03}F_4$, which undergoes difference luminescence transitions. Various non-radiative processes NRP are also shown by various curved or serpentine arrows. These arrows are labeled NRP in FIG. 3. FIG. 3 shows various state and wavelength transitions for exemplary EMR responsive dopants.

In FIG. 3, the solid arrows pointing up and labeled EP indicate the excitation pumping at 980 nm. The solid arrows pointing down and labeled TDF indicate temperature dependent fluorescence TDF transitions between 525 nm and 650 nm. Measurements of the intensity ratios between pairs of fluorescence transitions between 525 nm and 650 nm can be related to absolute temperature or relative temperature rise from initial base level. The active doping ions $Yb^{3+}$ and $Er^{3+}$ exhibit absorption in the wavelength regions of interest that is about 750 nm to about 765 nm, about 790 nm to about 815 nm and from about 1040 nm to about 1080 nm.

Figure 4:
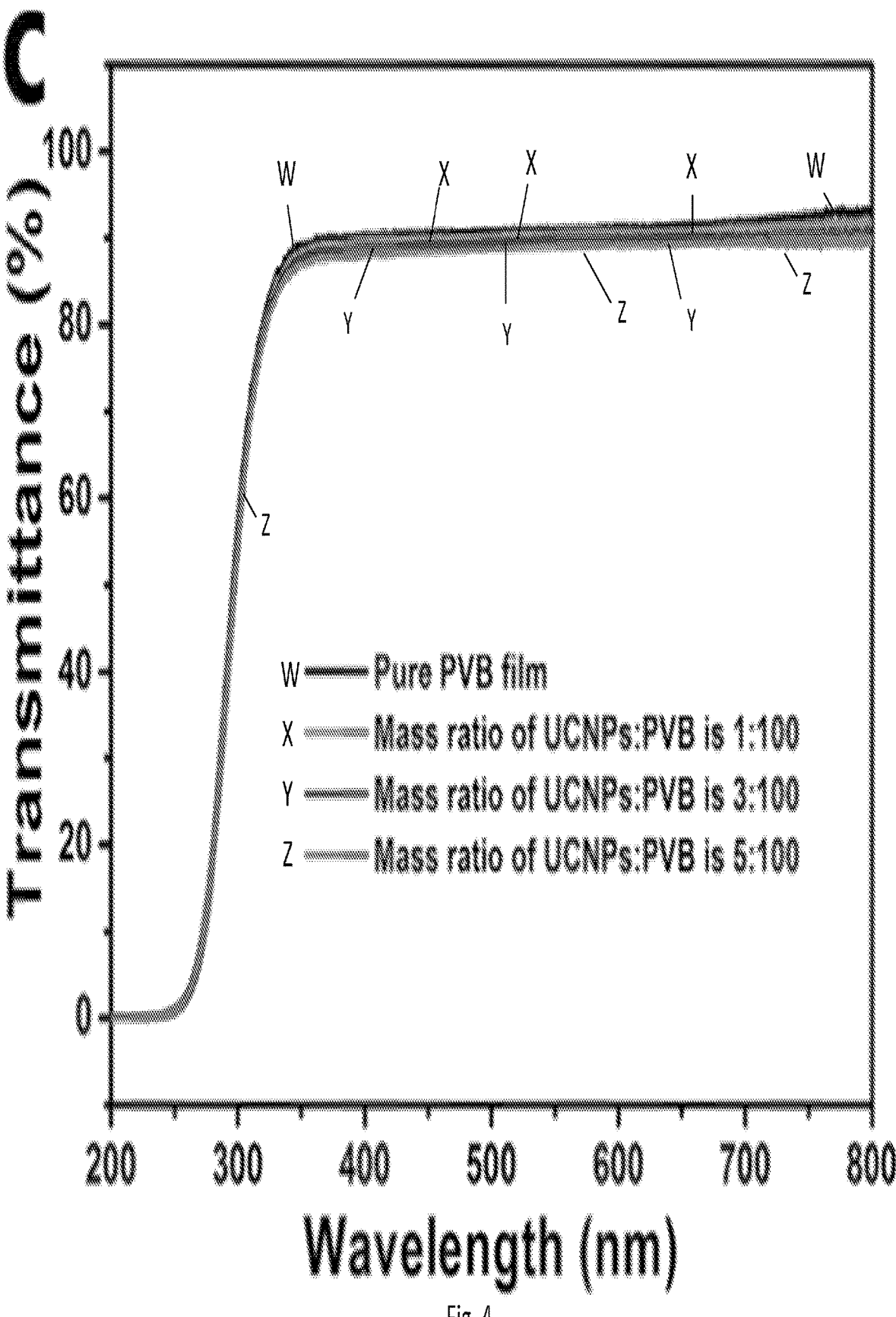
FIG. 4 is a plot of transmittance profile for polyvinyl butyral (PVB) film relative to various dopants (upconversion nanoparticles (UCNP)) of different mass ratios with respect to wavelength for exemplary EMR responsive dopants according to an illustrative embodiment of the disclosure.

The optical transmission of $NaY_{0.77} Yb_{0.20}Er_{0.03}F_4$ incorporated in polyvinyl butyral (PVB) film is plotted in FIG. 4. FIG. 4 shows transmittance spectra of the PVB film and the PVB/UCNPs hybrid films with different mass ratios of UCNPs:PVB (1:100, 3:100, and 5:100). In FIG. 4, the pure PVB film is shown by curve W (or black curve), which is the upper curve for the wavelength portion of the curve ranging from about 325 nm to about 800 nm. For this substantially flat portion of the transmittance plot, the next curve below the W curve is for the mass ratio of UCNPs:PVB of 1:100, which is plotted as X (or red). Similarly, the next curve below the X curve is for the mass ratio of UCNPs:PVB of 3:100, which is plotted as Y (or blue). Finally, the next curve below the Y curve is for the mass ratio of UCNPs:PVB of 5:100, which is plotted as Z (or green). The various plots of curves W, Z, Y, and Z show that the transmittance curve shifts below the pure PVB film as the ratio of UCNPs to PVB increases by mass.

The plot shows that the addition $NaY_{0.77}$ $Yb_{0.20}Er_{0.03}F_4$ of in the form of UCNP (rare-earth doped upconversion nanoparticles) in variable concentrations leads to very small changes in the transmission of the pure PVB (polyvinyl butyral) film. That plot demonstrates that $NaY_{0.77}$ $Yb_{0.20}Er_{0.03}F_4$ has very low optical absorption in the wavelength range between 400 and 800 nm. Other resins and optical films and materials may be used in various embodiments in addition or in lieu of PVB.

In addition, Yb and Er are poor EMR absorbers in the wavelength range from about 800 to about 850 nm and from about 1040 to about 1080 nm, which is not depicted in FIG. 4. It is expected that Yb and Er would poorly absorb in the about 800 to about 850 nm and from about 1040 to about 1080 nm wavelength range even if these ions were present in a different formulation or environment. There is a band between about 850 nm and about 1040 nm where Yb and Er may absorb the excitation radiation, but Yb and Er still have very low absorption in the wavelength bands of specific interest for aesthetic treatments, for example, from about 790 to about 815 nm and from about 1040 to about 1080 nm. In some embodiments, various wavelength ranges around about 980 nm may be used to pump EMR responsive dopants that include Yb and Er, either alone or together. Additional details and materials for selection as EMR-based dopant may be selected based on one or more of the criteria or requirements disclosed herein. In various embodiments, the properties of $NaY_{0.77}$ $Yb_{0.20}Er_{0.03}F_4$ and its temperature dependent fluorescence ratios make it suitable for use as a fluorescent material in the relatively thin contact liquid or gel between a solid heat sink, like sapphire and the skin.

For applications, like for example hair removal, that use relative thicker layer of water based gel on the surface on the skin, $NaY_{0.77}$ $Yb_{0.20}Er_{0.03}F_4$ may be used as an EMR responsive dopant in various embodiments. For example, in some embodiments, $NaY_{0.77}Yb_{0.20}Er_{0.03}F_4$ or other EMR responsive dopants may be included in a relatively thin layer of water based gel that is directly applied to the skin. In turn, the previously applied relatively thin gel layer that includes the EMR responsive dopant is coated with clear gel layer that does not include a fluorescent material or other EMR dopant. Multiple layers of gels, with and without EMR dopants, may be used in various combinations. In some embodiments, the clear gel is applied as an overcoat. The application of the second layer thicker gel overcoat may be performed without intermixing the thin or initial gel layer containing the EMR dopant with a subsequent layer of gel or other material that does not include the EMR dopant. Various EMR dopants may be used without limitation such as a suitable temperature dependent fluorescence material or other material disclosed or identified herein. In some embodiments, two gels are prepared as thin and thick patches that are sequentially applied on the skin before treatment. Further, in some embodiments using the application of two gels of differing thickness, viscosity, or other parameters, the thin first patch (or portion) to be applied contains the fluorescent material with temperature dependent fluorescence, and the second thicker patch (or portion) without fluorescent material provides extra heat sink mass.

Disclosed here is an electromagnetic radiation delivery and monitoring system for non-invasive surface tissue temperature monitoring. Suitable surface tissues that may be monitored by this system include external skin surfaces being treated for unwanted pigment, hair, vascular lesions, tattoos, and adipose tissue. Other surfaces that may be monitored by this system include mucosa for example, oral, vaginal, anal, nasal, and ophthalmic as well as eyelid and ear surface tissue. Other surfaces that may be monitored by this system include tissues accessible via surgery, either open or endoscopic surgery.

Endogenous Fluorescence Chromophores

There is no data demonstrating temperature dependent fluorescence from chromophores naturally present in the epidermis like melanin or water. If future research demonstrates temperature dependent fluorescence from epidermal chromophores, it would allow for a convenient extension of the concept of real time temperature monitoring based on temperature dependent fluorescence.

Real Time Skin Temperature Monitoring and Related Signal to Noise Improvements

During light-based treatments practitioners prefer to see fine skin details in the area of the skin that they are treating. For example, subtle changes in skin coloration may be used by experts as feedback that informs changes in or termination of a given treatment. The present commercially available light-based technology offers unobstructed view of the treatment area. Treatments are usually performed under operating room illumination. In addition, some practitioners use head mounted illumination devices.

A real time skin temperature monitoring system based on up-conversion materials emitting temperature dependent fluorescence may be adversely affected by the existing illumination in the operating room. For example, the fluorescent material $NaY_{0.77}$ $Yb_{0.20}Er_{0.03}F_4$ has temperature dependent fluorescence emission bands in the green wavelength range of between about 525 nm and about 540 nm and in the red wavelength ranged of about 650 nm. Incandescent or LED lights are often used to illuminate a treatment room and the operating field. With respect to both of these types of lights, the wavelength ranges used for illumination overlap with the fluorescent bands of the up-conversion materials that emit temperature dependence fluorescence that is used in certain light-based tissue treatments. These wavelength bands can result in undesirable measurement errors by overlapping with the signal generated in response to the heating of fluorescent material being used for tissue temperature monitoring during a cosmetic or other tissue treatment. In particular, detecting a fluorescence based signal indicative of tissues or temperature changes may be washed out or otherwise combined with noise as a result of light being used to illuminate the room or a treatment region.

Specifically, the overlap of the room illumination with the temperature dependent fluorescence emission bands may lead to incorrectly calculated temperature or the inability to calculate a sufficiently accurate tissue temperature. For example, when the temperature is calculated from the ratio of the intensity of temperature dependent fluorescence emission bands that ratio will be affected by in band intensity added by the room lights. Typically, the room lights are not expected to produce biologically significant heating and temperature rise in the treatment area.

In various embodiments, a wavelength selective filter may be positioned relative to one or more optical components or applicators of a treatment head or applicator and a detector such as detector FD. For example, in one embodiment, a band pass filter can be positioned in front of the fluorescent optical detector in order to reduce, attenuate, and/or filter optical wavelengths from one or more lights that are outside of the fluorescent band(s) of interest. The use of such a filter may be configured such that wavelengths that are outside of the fluorescent band(s) of interest are modified to have a negligible intensity and thus limit their impact on any optical detectors used in a given cosmetic or monitoring system. In various embodiments, a given wavelength filter is used to prevent out-of-band noise from reaching the optical detector of a treatment system.

In some embodiments, the fluorescent signal detector is disposed in a housing that prevents light from entering other than through an aperture this is disposed along a light path to receive the temperature dependent fluorescent emission that encodes tissue temperature information. In some embodiments, the wavelength selection filter is disposed in front of, behind, or aligned with the aperture. The use of a housing and an aperture may be used to prevent the optical detector from being flooded with unfiltered light that overlaps with the temperature dependent fluorescent signal from the fluorescent material. In some embodiments, the wavelength selective filter is tuned to a specific narrow wavelength band that is centered around or includes the wavelengths generated by the excitation of the fluorescent material.

In some embodiments, the room illumination that passes through the band pass filter in front of the fluorescent detector would represent a background noise signal that cannot be filtered optically. For example, that may happen if the room illumination has high intensity in the green and red bands mentioned above. Blocking the room illumination from reaching the treatment area would be a substantial inconvenience for the practitioner. As a result, Applicants have determined that systems and methods that reduce the impact of room illumination and other lights are preferably incorporated into a given monitoring or treatment system. Various embodiments avoid modifying room lights or including light blocking shields or coverings that are likely to interfere with an operator's ability to visually inspect a region being monitored or treated.

In various embodiments, it is desirable to increase the signal to noise ratio of the light being delivered from the up conversion temperature sensing materials to the optical detector while in the presence of the room lights. In some embodiments, the peak power of the temperature dependent fluorescence excitation laser is increased by a percentage or multiplier. For various embodiments, the peak power of the laser or source of excitation energy is increased by a factor of about 10. For example, in some embodiments a peak power per unit area for a fluorescence excitation source with wavelengths of about 980 nm is less than about 100 W/cm². In various embodiments, the peak power per unit area is less than about 50 W/cm². In many other embodiments, the peak power per unit area is less than about 20 W/cm². In some embodiments, the peak power per unit area ranges from about 5 W/cm² to about 30 W/cm².

In various embodiments, the peak power is increased while pulsing the laser or fluorescence excitation source with a low duty cycle. Typically, for periodic pulsing sources, duty cycle is defined as the fraction of one period in which the source is active. The fraction is commonly expressed as percentage. The period, T, for a periodic pulsing source is the inverse of the frequency, f, (T=1/f or f=1/T). In some embodiments, a low duty cycle is less than about 40%. In some embodiments, a low duty cycle is less than about 20%. In many embodiments, a low duty cycle is less than about 10%. For example, an excitation source pulsed with on-time of up to about 40 ms at a rep-rate up to about 2 Hz would result in about 8% duty cycle for the excitation source (0.04 seconds×2 Hz=0.08=8%). These are typical values for an example application of laser hair removal in accordance with the disclosure. In various embodiments, a combination of an increase in peak power and a decrease in duty cycle may be selected so that the average excitation power stays low.

For example, in some embodiments a low average power per unit area for a fluorescence excitation source with wavelengths around 980 nm is less than about 10 W/cm². In various embodiments, a low average power per unit area is less than about 5 W/cm². In various embodiments, a low average power per unit area is less than about than 2 W/cm². In some embodiments, the low average power per unit area ranges from about 2 W/cm² to about 15 W/cm². The choice for the average power per unit area for the fluorescence excitation source is selected in various embodiments such that it generates a biologically insignificant temperature rise in the treatment area.

Additional design features may be used to adjust one or more parameters of the fluorescence excitation source or the temperature dependent fluorescence material. Specifically, various features and parameters may be modified if the higher power short fluorescence excitation pulses lead to saturation or bleaching of the up-conversion effect in the fluorescent material or fluorescent nano-particles or optical damage effects. For example, optical damage effects could be changes in the optical or fluorescent properties of the fluorescence material that may result in temperature calculation errors. In various embodiments, selecting the temperature dependent fluorescence material may address issues related to saturation or bleaching of the up-conversion effect or optical damage effects.

In some embodiments, the excitation laser power used in a temperature dependent fluorescence monitoring may range from about 1 to about 2 W/cm². A higher power fluorescence excitation laser can be used to generate a larger temperature dependent fluorescence signal in pulse mode with low duty cycle to avoid unnecessary heating of the fluorescent material and the skin. The higher power fluorescence excitation laser may lead to a higher fluorescent signal. As a result, the low duty cycle of the fluorescence excitation laser is selected to produce biologically insignificant heating. In turn, this limits the temperature rise in the treatment area. For example, a fluorescence excitation laser having a power that ranges from about 10 W/cm² to about 20 W/cm² excitation laser system may be used in some embodiments.

In various embodiments, the fluorescence excitation laser is pulsed with on-time of up to 40 ms at a rep-rate up to 2 Hz (these are typical values for an example application of laser hair removal and lead to up to 8% duty cycle for the irradiation laser). The pulse on-time or pulse duration of the fluorescence excitation laser may be chosen to start shortly before the delivery of the treatment laser pulse so that a baseline temperature can be measured immediately before the treatment pulse. After the baseline temperature reading, the fluorescence excitation laser energizes the fluorescent material for the duration of the treatment pulse. In this way, the use of the excitation light during a given monitoring or treatment session provides real-time temperature measurement over the course of a given session.

In some embodiments, temperature measurements may be improved by extracting the temperature dependent fluorescent signal from the room illumination noise with the use of one or more signal processing devices. In some embodiments, a lock-in amplifier may be used. A lock-in amplifier allows the extraction of a useful weak signal from a large noise background. A lock-in amplifier takes the input signal from the fluorescence signal detector, multiplies it by the synchronous reference signal, and integrates it over a specified time period.

In various embodiments, the reference signal is provided from the fluorescence excitation laser or its driver or its optical modulator. In many embodiments, given the multiplication and integration performed, the resulting output signal is a DC signal. One advantage of using a lock-in amplifier is that the contribution from an input signal that is not at the same frequency as the synchronous reference signal, e.g. the room lights, is attenuated close to zero. In various embodiments, the lock-in amplifier allows the low intensity temperature dependent fluorescent signal to be measured against the background of the room lights noise signal. By reducing the noise contribution of the room lights, the lock-in amplifier increases the signal to noise ratio of the temperature dependent fluorescent signal. In turn, this improves the accuracy of temperature readings obtained using the fluorescent signal.

In some embodiments, the specified time period over which the integration is performed ranges from about 1 milliseconds to about 1000 milliseconds. In some embodiments, the system includes a phase-locked loop (PLL) that locks to the reference frequency and supplies the reference frequency to the lock-in amplifier. In some embodiments, the lock-in amplifier includes a multiplier, a phase-sensitive detector, one or more filters, an integrator, and various other components. In some embodiments, a low pass filter or other filter is used to remove various noise frequencies that are not associated with the reference frequency. In some embodiments, the lock-in amplifier multiples the fluorescent light signal that is correlated with skin temperature with sine wave and measures the Fourier component of the signal at the reference frequency.

Figure 5:
FIG. 5 is a schematic diagram of an exemplary EMR delivery system suitable for performing real time temperature monitoring of a tissue region according to an illustrative embodiment of the disclosure.

An example block-diagram of a system that includes a control system and a fluorescent signal detection (FSD) system is shown in FIG. 5. In various embodiments, the FSD system includes detector FD and a lock-in amplifier. In various embodiments, the control system triggers the fluorescent excitation source to activate the fluorescence excitation beam with a modulation frequency $f_m$. The modulation frequency is supplied also to the FSD system as a synchronous reference input to the lock-in amplifier. In some embodiments, the range of modulation frequencies, $f_m$, for pulsing the fluorescence excitation source is from about 100 Hz and to about 100 MHz. In various embodiments, $f_m$ ranges from about 100 Hz to about 100 kHz.

In some embodiments, the FSD system determines the pre-treatment skin temperature using the lock-in amplifier, the temperature dependent fluorescent signal and the signal modulated using the modulation frequency $f_m$. The FSD system sends the pre-treatment skin temperature data to the control system. If the control system determines that the pre-treatment skin temperature is within the expected range, the treatment beam source is activated for a pre-set period of time. During delivery of the treatment beam, the FSD system continuously monitors and determines the skin temperature. Real time skin temperature values or the underlying data are obtained and transmitted to the control system. In various embodiments, the control system uses or determines changes in temperature measured using signals received from the fluorescent material to generate various responsive outputs.

For example, in some embodiments, if the control system determines that the skin temperature is approaching the upper boundary of the safety range, the control system may alert the operator with visual, sensory, or auditory alerts. In some embodiments, the control system may stop delivery of the treatment beam in response to one or more temperature values, thresholds or ranges that are correlated with fluorescent signals from the FnPg layer.

Exemplary Upconversion Materials and Thermometry

In various embodiments, luminescence thermometry may be used along with various compounds and materials as described herein. These compounds and materials may be selected based on changes in intensity, linewidth, photoluminescence lifetime, or spectral shifts. In some embodiments, lanthanide ions are used in the various temperature sensing applications described herein because of their stability and narrow spectral features that enable distinguishing changes easily. Lanthanide-doped materials display upconversion luminescence: they can be excited with near-infrared (NIR) light, and emit in the visible region of the spectrum. NIR excitation induces less self-absorption and scattering by biological tissue; therefore remote excitation is easier. In various embodiments, upconversion nanoparticles (UCNPs), inorganic nanoparticles doped with lanthanide ions, and others may be used as cream, topical, or otherwise applied to a subject.

Materials that include a lanthanide-doped phosphor such as $NaY_{0.77}Yb_{0.20}Er_{0.03}F+$ and others may be used to perform luminescence thermometry and used as a component in the gels, creams, layers, and other materials disclosed herein. In some embodiments, two or more 980 nm photons are used to induce emission in the visible. Besides direct excitation of the $Er^{3+}$ ion, there is energy transfer from excited $Yb^{3+}$ to excited states of $Er^{3+}$. Emission is in the blue, green and red regions of the visible spectrum depending on the upper $Er^{3+}$ level in the transition. Upconversion thermometry often focuses on the two transitions emitting at 525 nm and 540 nm, i.e. $^2H_{1/2} \rightarrow ^4I_{15/2}$ and $^4S_{3/2} \rightarrow ^4I_{15/2}$. The $^2H_{11/2}$ and $^4S_{3/2}$ levels are closely spaced in energy so they are effectively in thermal equilibrium. Their population ratio can therefore be expressed or modeled by a Boltzmann distribution:

$$\frac{N_i}{N_S} = C \exp\left(\frac{-\Delta E}{kT}\right)$$

where $N_i$ is the population in level i, $\Delta E$ is the spacing between the levels, k is Boltzmann's constant and C is a constant depending on degeneracies.

Based on this, the ratio of 525 nm and 540 nm luminescence intensities, RHS, can be used to infer the ratio of $^2H_{11/2}$ to $^4S_{3/2}$, which gives the temperature of the sample. In some embodiments, temperature-dependent upconversion luminescence results for $NaY_{0.77} Yb_{0.20}Er_{0.03}F_4$ may be obtained using a spectrometer coupled to a temperature stage.

The terms "about" and "substantially identical" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by $1/10$ of the stated value, e.g., $\pm 10\%$. For instance, applying a voltage of about +3V DC to an element can mean a voltage between +2.7V DC and +3.3V DC. Likewise, wherein values are said to be "substantially identical," the values may differ by up to 5%.

Whether or not modified by the term "about" or "substantially" identical, quantitative values recited in the claims include equivalents to the recited values, e.g., variations in the numerical quantity of such values that can occur, but would be recognized to be equivalents by a person skilled in the art.

All of the drawings submitted include one or more ornamental features and views, each of which include solid lines any of which also incorporate and correspond to and provide support for dotted lines and each of which include dotted lines any of which also incorporate and correspond to and provide support for solid lines.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

Using the terms "include," "includes," "including," "have," "has," or "having" should be generally understood as open-ended and non-limiting unless specifically stated otherwise.

Using the singular herein includes the plural (and vice versa) unless specifically stated otherwise. The singular forms "a," "an," and "the" include plural forms unless the context dictates otherwise. In addition, where using the term "about" is before a quantitative value, the present teachings also include the specific quantitative value itself, unless specifically stated otherwise.

It should be understood that the order of steps or order for performing certain actions is immaterial if the present teachings remain operable. Two or more steps or actions may be conducted simultaneously.

Where a range or list of values is provided, each intervening value between the upper and lower limits of that range or list of values is individually contemplated and is encompassed within the disclosure as if each value were specifically enumerated. In addition, smaller ranges between and including the upper and lower limits of a range are contemplated and encompassed within the disclosure. Listing exemplary values or ranges is not a disclaimer of other values or ranges between and including the upper and lower limits of a range.

It should be appreciated that numerous changes can be made to the disclosed embodiments without departing from the present teachings. While the foregoing figures and examples refer to specific elements, this is intended to be for example and illustration only and not by way of limitation. It should be appreciated by the person skilled in the art that various changes can be made in form and details to the disclosed embodiments without departing from the teachings encompassed by the appended claims.

What is claimed:

1. An electromagnetic radiation (EMR) delivery and monitoring system for non-invasive surface tissue temperature monitoring comprising a first source of EMR having a first wavelength range;

a second source of EMR having a second wavelength range; and a tissue contacting material comprising a set of wavelength range specific EMR responsive dopants, wherein the tissue contacting material is configured to be positioned on a surface of a target region of tissue, wherein the tissue contacting material receives EMR from the first source at a first orientation, wherein the tissue contacting material receives EMR from the second source at a second orientation.

2. The system of claim 1, wherein the first orientation and the second orientation are the same.

3. The system of claim 1, wherein the second orientation is at an angle relative to the first orientation.

4. The system of claim 1, wherein the first source of EMR generates a treatment beam.

5. The system of claim 4, wherein the second source of EMR generates an excitation beam.

6. The system of claim 1, wherein the EMR responsive dopants are selected from the group consisting of a particle, a bead, a layer, a thin film, a fluorescent material, a fluorescent nanoparticle, an upconversion fluorescent nanoparticle, an upconversion material, a nanoparticle, a chromophore, a scattering element, a refracting element, a wavelength shifting material or device, interference generator, absorber and combinations thereof.

7. The system of claim 1, wherein the EMR responsive dopants comprise two or more fluorescent materials.

8. The system of claim 1 further comprising a signal processor, wherein the signal processor is operable to measure temperature changes using received temperature dependent EMR from one or more dopants and one or more parameters of the EMR generated from the second EMR source.

9. The system of claim 8, further comprising a control system operable to stop treatment or generate an alarm when a tissue temperature exceeding a threshold or predetermined value has been detected using EMR from the dopants.

10. The system of claim 1 wherein the EMR responsive dopants are temperature sensitive such that tissue temperature changes in tissue in contact with the tissue contacting material cause changes in EMR emitted or transmitted from the EMR responsive dopants.

11. The system of claim 1, further comprising a wavelength selective filter configured to filter one or more wavelength bands of room or treatment radiation while transmitting the temperature dependent EMR generated from one or more of the dopants.

12. The system of claim 1, wherein the second source of EMR generates an excitation beam, wherein the excitation beam has a modulation frequency fm.

13. The system of claim 12, further comprising a lock-in amplifier having a reference frequency, wherein the reference frequency is the modulation frequency fm.

14. The system of claim 1, wherein the second source of EMR generates a pulsed excitation beam and the first source of EMR generates a treatment beam.

* * * * *